United States Patent [19]

Barkalow et al.

[11] 4,198,963
[45] Apr. 22, 1980

[54] CARDIOPULMONARY RESUSCITATOR, DEFIBRILLATOR AND MONITOR

[75] Inventors: Clare E. Barkalow, Comstock Park, Mich.; James O. Elam, Chicago, Ill.

[73] Assignee: Michigan Instruments, Inc., Grand Rapids, Mich.

[21] Appl. No.: 952,656

[22] Filed: Oct. 19, 1978

[51] Int. Cl.² ............................................. A61H 31/00
[52] U.S. Cl. .............................. 128/53; 128/419 D; 128/642; 128/802
[58] Field of Search .............. 128/28, 53, 419 D, 642, 128/284, 785, 786, 798, 802

[56] References Cited

U.S. PATENT DOCUMENTS

| 3,326,207 | 6/1967 | Egan | 128/642 |
|---|---|---|---|
| 3,461,860 | 8/1969 | Barkelow | 128/53 |
| 3,461,861 | 8/1969 | Barkelow et al. | 128/53 |
| 3,716,059 | 2/1973 | Welborn et al. | 128/419 D |
| 3,837,347 | 9/1974 | Tower | 128/785 |
| 4,082,090 | 4/1978 | Harrigan | 128/28 |
| 4,088,138 | 5/1978 | Diack et al. | 128/419 D |
| 4,090,518 | 5/1978 | Elam | 128/351 |

OTHER PUBLICATIONS

Schaudinschky et al., "Medical and Biological Engineering", vol. 7, No. 3, May 1969, pp. 341–343.

Primary Examiner—William E. Kamm
Attorney, Agent, or Firm—Price, Heneveld, Huizenga & Cooper

[57] ABSTRACT

A reciprocal cardiac compressor is provided for cyclically compressing a patient's chest. The cardiac compressor includes a resuscitator for ventilating the patient's lungs. A first internal electrode is positioned in the esophagus of the patient with an esophageal-pharyngeal airway. The resuscitator ventilates the patient's lungs through the esophageal-pharyngeal airway. The cardiac compressor includes a compressor pad positioned anterior to the patient's heart for compressing the patient's sternum and heart. An external electrode is disposed on the face of the compressor pad for compression between the compressor pad and the patient's sternum. A cardiac defibrillator is connected between external and internal electrodes for establishing a defibrillating electric current therebetween. A monitor is connected to the external and internal electrodes for monitoring the electrical activity of the patient's heart. Means for synchronizing the defibrillator and the compressor is provided comprising a pressure sensitive switch for synchronizing the defibrillator and compressor such that defibrillating current is applied to the patient's heart only during a systolic portion of the compression cycle of the compressor.

36 Claims, 14 Drawing Figures

CARDIOPULMONARY RESUSCITATOR, DEFIBRILLATOR AND MONITOR

BACKGROUND OF THE INVENTION

This invention relates generally to cardiopulmonary resuscitation defibrillation and monitoring apparatus and, more particularly, to a combination cardiac compressor, lung ventilation, defibrillator and heart monitor apparatus.

External cardiac compression can be effectively employed for obtaining perfusion by causing forced pumping of blood from a temporarily stopped heart. This is achieved by constant cyclic external compression of the heart (systole) for a short time period followed by pressure release to allow heart expansion (diastole) for a short time period. To achieve proper heart compression by external force, the breast bone is forced toward the backbone of the patient while the patient's back is rigidly supported.

Although forced pumping of blood is essential for a patient whose heart has failed, this is only part of the continuous treatment necessary, since when the heart fails, breathing normally fails also. Hence, when external mechanical or manual cardiac compression is presently employed, simultaneous, sustained cyclic, mechanical or mouth to mouth ventilation is also important to cyclically inflate the lungs for oxygenization of the blood. According to accepted medical practice, the lungs are ventilated or inflated during the diastole period of the compression cycle. Whether carried out mechanically or manually, these techniques comprise what is commonly referred to as cardiopulmonary resuscitation or CPR. However, CPR is only supportive therapy designed merely to maintain cell viability or structure. CPR alone will normally not restart a heart that has stopped or which is in ventricular fibrillation. Definitive therapy such as defibrillation by electrical shock is normally necessary to restart the normal functioning of the heart.

In the prior art, certain disadvantages existed when such supportive and definitive therapy were combined. When applying supportive therapy, it is extremely important that there be no interruptions. In the case of manual CPR where chest compression is being performed manually by the application of force by the rescuer's hands, interruptions are presently necessary to monitor the patient's EKG and to apply electrical defibrillation shocks. In the first case, supportive therapy must be interrupted because of distortion in the patient's EKG produced by the rescuer. This distortion or noise is generated from the rescuer's own EKG and from electrical signals generated in the rescuer's muscles as he applies chest compression. This distortion or noise is high enough to completely obscure the patient's EKG and must be interrupted during the time that the patient's EKG is being assessed. This is an interruption which is inevitable in the manual CPR technique. Furthermore, if the patient requires electrical defibrillation, then at that time, in the manual technique, the hands must be taken off because of the risk of giving a shock to the rescuer. Also, generally speaking, after a heavy external defibrillation shock, a substantial time period must pass before the oscilloscope and the circuitry within the oscilloscope or chart of the EKG monitor returns to normal. Sometimes it takes several seconds for the equipment to clear and provide a check on the electrical activity of the patient's heart and during this time, the patient is left unmonitored.

When using one of the many standard commercially available mechanical massagers, there is often room on the chest to place defibrillation paddles while external cardiac compression is being performed. If the compressor is pneumatic rather than electrically driven, distortion in the patient's EKG is minimal and a useful signal can be obtained without interruption in supportive therapy. Thus, it is possible to give defibrillation shocks while such a CPR unit is running. However, for some reason there has been a reluctance on the part of rescuers to use this technique, and rescuers in the past have had a tendency to shut the CPR unit off during defibrillation and monitoring. This is probably due to the fact that the rescuer carrying out the operation would be standing over the patient with some risk of his being in contact with the equipment or with the patient. Thus, even though distortion caused by pneumatically driven CPR equipment is minimal and the signal normally obtained during CPR is adequate to make a judgment as to whether the patient is in cardiac arrest or not, most rescuers insist on shutting off CPR equipment during defibrillation and monitoring.

The most common definitive therapy in the prior art is the use of a defibrillation shock for restarting a heart that has stopped or a heart that has gone into ventricular fibrillation. However, the conventional external electrodes used in the prior art are placed on the patient's chest and a disproportionately large amount of the current applied to the patient's chest never flows through the heart. Accordingly, the power requirements of prior art defibrillators are quite high and most prior art units are bulky and ill-suited to portability. Thus, it is often not possible to apply such definitive therapy to the patient until the patient has reached a hospital. Furthermore, since a disproportionate amount of energy must be applied to the patient's chest to cause that small percentage of electrical energy flowing through the heart to be sufficient to defibrillate the heart, electrical defibrillation, as carried out in the prior art, with external electrodes, is a traumatic event both for the heart and other portions of the patient's body.

Esophageal obturator airways are commonly used in the prior art to prevent aspiration of the contents of the patient's stomach during resuscitation. Although it has been suggested in the prior art to place monitoring and defibrillation electrodes within the esophagus of a patient with such an esophageal obturator to improve monitoring and defibrillation techniques, these arrangements do not solve the aforementioned problem of interrupting supportive techniques during monitoring or defibrillation.

SUMMARY OF THE INVENTION

These and other problems in the prior art are solved by provision of a cardiac compressor and defibrillator comprising a reciprocal cardiac compressor for cyclically compressing a patient's chest. The cardiac compressor includes an external compressor pad normally positioned anterior to the patient's heart such that the pad contacts the patient's sternum. An external electrode is disposed on the face of the compressor pad for compression between the compressor pad and the patient's sternum. A first internal electrode is disposed in the patient's esophagus and means for positioning the internal electrode posterior to the patient's heart is provided. A cardiac defibrillator is connected to the external and internal electrodes for establishing a defibrillating electric current therebetween. Means are provided for synchronizing the defibrillator and compressor, whereby defibrillating current is applied to the patient's heart only during a systolic portion of the compression cycle of the compressor.

With this arrangement, supportive therapy remains uninterrupted during such definitive therapy as monitoring and the application of electrical defibrillation shock. Furthermore, since electrical defibrillation shocks are now applied with internal and external electrodes during the systole, or the point of maximum compression during the compression cycle, a dramatic reduction in the power requirements of the defibrillator is achieved. This reduction in the power requirements of the defibrillator is achieved since internal and external electrodes are centered over the heart and power is applied while these electrodes are compressed on the heart such that the current applied is directed specifically through the myocardium of the heart. With the electrodes so positioned during the systole portion of the compressor cycle, almost all of the current applied therebetween flows through the heart. Thus, a relatively small amount of electrical energy need now be applied to generate a sufficient defibrillation current in the heart, and electrical defibrillation becomes a much less traumatic event, both to the heart muscle and to other parts of the body. Furthermore, the reduction in the power requirements of the defibrillator makes possible much smaller, simpler, lighter and more portable lower power defibrillators that are less expensive and which may be easily carried on site by the rescuer. In fact, it is possible with such a technique, even to provide defibrillators that operate from rechargeable nickel cadium batteries or the like.

In general, as monitoring electrodes are placed closer to the heart, stronger monitoring signals and higher signal noise ratios are achieved. The internal esophageal electrode working in conjunction with the massager electrode give an extremely strong, large, very clean signal suitable for monitoring the heart and identifying gross arrhythmias such as ventricular fibrillation. Therefore, monitoring of the heart for gross arrhythmias and periodic defibrillation of the heart may be carried out without interruption of supportive therapy such as cardiac compression and ventilation of the lungs.

DESCRIPTION OF THE PREFERRED EMBODIMENTS

Figures 1, 2, 3, 4, 5:
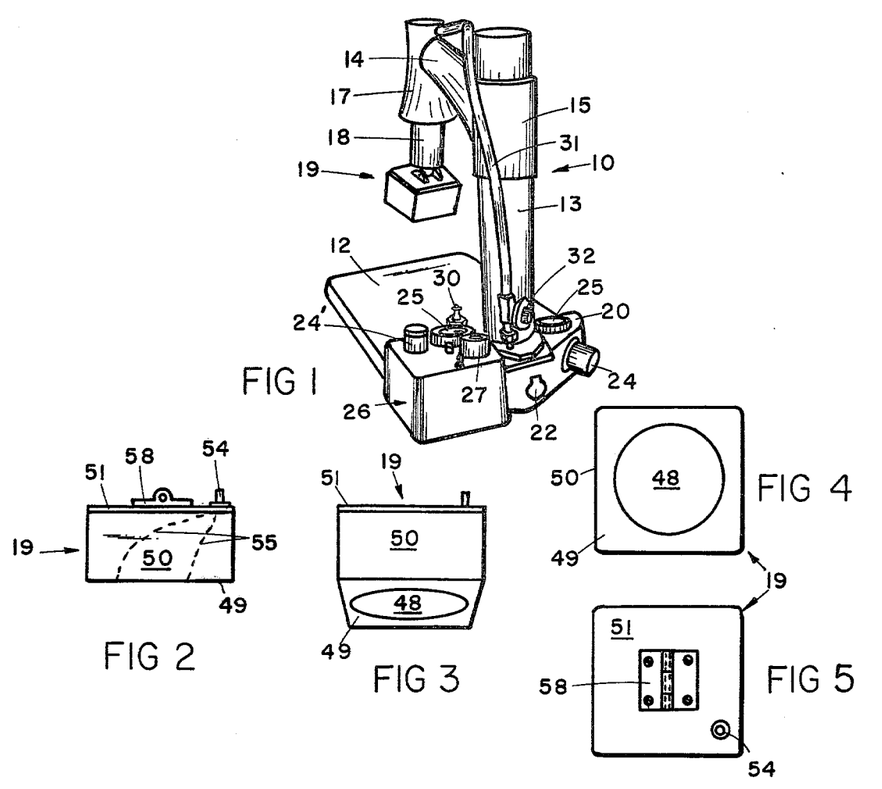
FIG. 1 is a perspective view of a pneumatically operated combined cardiac compressor and ventilator of the present invention.
FIG. 2 is an elevational view of a compressor pad constructed according to the present invention.
FIG. 3 is a perspective view of a compressor pad constructed according to the present invention.
FIG. 4 is a bottom view of a compressor pad constructed according to the present invention.
FIG. 5 is a top view or plan view of a compressor pad constructed according to the present invention.

Referring now to FIG. 1, a combination cardiac compressor and ventilator or cardiopulmonary resuscitator unit is illustrated at 10. The CPR unit includes a platform 12 for supporting the back of a patient, a removable upstanding column or support 13 and an overhanging beam or arm 14 mounted to column support 13 with a releasable collar 15. The outer end of arm 14 includes a pneumatic power cylinder 17, an extendable plunger piston 18 and a compressor pad 19 for contacting and compressing a patient's sternum. The piston plunger 18 and the compressor pad 19 are pneumatically operable to shift towards the platform 12 to compress the sternum and thus the heart of the patient resting in the supine position on the platform 12. The piston and pad return with the normal expansion of the patient's chest. The platform 12 includes a thick hollow end 20 in which the support 13 is removably mounted and which includes an internal chamber that encloses a control valve assembly at 22. The control valve assembly repetitively applies pressure to the power cylinder to create a cyclical compression cycle. Protruding from the platform portion 20 is a pressure regulator knob 24 for controlling the pressure of the output of control valve assembly 22. A pressure indicating gauge is disposed at 25. A ventilator subassembly is disposed at 26 and is integrally mounted with the compressor with the exception of an air hose normally connected to air outlet 27 and a mask or tube for directing oxygen enriched air into the patient's lungs. A pressure regulator knob 24′ and a gauge 25′ are used to control the air pressure applied to the patient's lungs during ventilation. The CPR unit used herein is essentially like that shown in U.S. Pat. No. 3,461,860 to Clare E. Barkalow and the disclosure of that patent is incorporated herein by reference.

The cardiac compressor operates at a relatively high pulse rate. The ventilator operates at a much slower pulse rate. For example, a ratio of compressor to ventilator cycles is commonly 5:1. When combining the two, means is provided to cause a ventilation cycle to occur only every multiple of compressor cycles. The compressor cycles are controlled by the aforementioned control valve 22. Only periodic output pulses of oxygen from the control valve are allowed to pass to the ventilator 26. The duration of each pulse of oxygen to the ventilator is regulated by a timer control.

One of the advantages of this type of apparatus is that both the cardiac compressor and the ventilator of the CPR unit are pneumatically operated and pneumatically controlled. Once the device is set up, the only power source required is an external source of compressed gas, normally oxygen, which is connected to the unit via a gas hose attached to fixed connector 30. This supply of pressurized oxygen operates the entire CPR unit. Pressurized oxygen passes through the compressor control valve assembly 22, inside the cardiac compressor platform, and then through air hose 31 that extends to the upper end of cylinder 17. A manual shut-off valve 32 may be provided to turn off the cardiac compressor manually while allowing the ventilator unit 26 to still operate on a cyclical basis. Oxygen also passes to a programmer, not illustrated, that is a pneumomechanical device serving to periodically open a passageway for a flow of oxygen to the ventilator at regular intervals after a specific number of compression cycles of the cardiac compressor. The programmer acts to create a pulsing pressure bleedoff from the conduit 31 extending to the cardiac compressor cylinder 17. The programmer can be preset to provide pulses of oxygen to the ventilator at regular multiples of intervals, usually 1 out of 5 of the cardiac compressor cycles, since the lungs should be ventilated only once every multiple of cardiac compressions. According to the presently accepted medical teachings, the programmer is normally set to create a pulse of oxygen to the ventilator during cardiac diastole, that is, when compressor cylinder pressure is zero and the chest is free to expand. When the ventilator program determines that the correct number of compression cycles has passed, a flow of ventilating oxygen occurs from outlet 27 which is directed into the patient's lungs with a mask, tube or the like and an interconnecting hose. Further details of the structure and operation of a CPR unit suitable for use with the present invention may be obtained from the aforementioned Barkalow patent.

Figure 6:
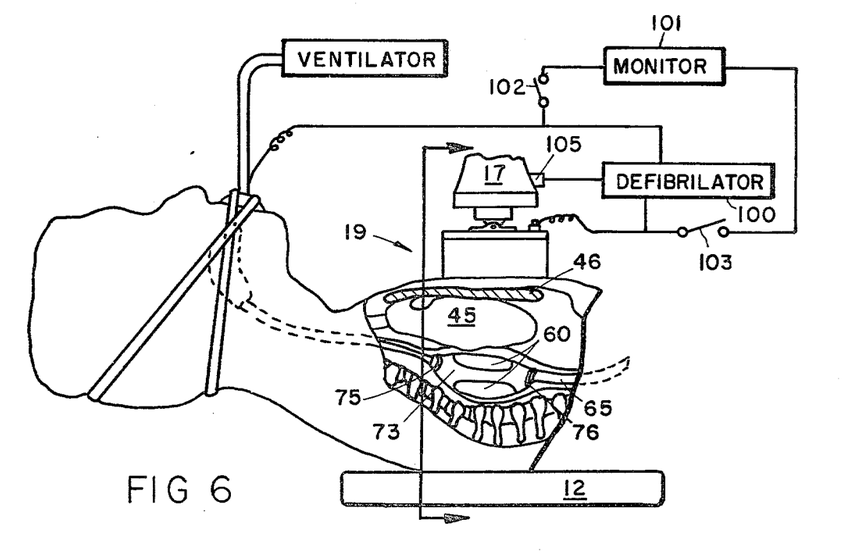
FIG. 6 is a schematic representation of the cardiopulmonary resuscitator defibrillator and monitor of the present invention and a fragmentary sagital section illustrating the application of the present invention to the human body.

Referring now also to FIGS. 2, 3, 4 and 5, details of the external cardiac compressor pad 19 of the present invention are illustrated. The cardiac compressor pad 19 is connected to and is actuated by the CPR unit 10 for compressing the patient's sternum and thus compressing the patient's heart between the sternum and spine. The compressor pad 19 as best illustrated in FIG. 6, is positioned anterior to the patient's heart 45 in contact with the lower portion of the patient's sternum 46. An external electrode 48 is disposed on a face 49 of the compressor pad 19 for compression between the compressor pad 19 and the patient's sternum 46. The body 50 of the compressor pad 19 is preferably molded from a flexible closed cell integral skin polyurethane foam. The body 50 is mounted on a planar support 51. The face 49 of the compressor pad 19 preferably extends over an area greater than that of conventional external compressor pads and an area much greater than the manual "heel of hand" contact area normally available when the manual CPR technique is applied. The area of face 49 is preferably approximately eight times larger than the normal manual "heel of hand" contact area.

The external electrode 48 covers a relatively large area of the face 49 and is preferably ten square inches or more in area. Electrode 48 is isolated electrically from all metal parts of the CPR assembly except that it is electrically connected to a terminal 54 disposed at the top of the assembly by multiple internal flexible leads shown in phantom at 55 in FIG. 2. The electrode 48 is preferably flexible to conform to the shape of the patient's chest and sternum and a metal mesh screen electrode vulcanized to the face 49 of the compressor pad 19 is preferred. Gold plated brass mesh screens and silver mesh screens have both been found suitable. However, a suitable conductive elastomer may also be employed for the body 50 of compressor pad 19, or for at least the face 49 of the body 50 to act as the electrode 48.

The planar support 51 for the body 50 of compressor pad 19 includes a hinge or pin-type connection 58 so that the compressor pad 19 may be pinned to the piston 18 of the CPR unit 10. This hinged connection is preferable since the patient's sternum 46 is not always horizontally oriented when the patient is in the supine position as illustrated in FIG. 6. This hinged, or pinned connection allows the compressor pad 19 to more closely follow or conform to the patient's chest. In an effort to further reduce the trauma of external cardiac compression and to increase the compliance and conductivity of electrode 48, the base 49 of the body 50 of compressor pad 19 is preferably molded to conform to the outline of a typical human chest. The body 50 of flexible foam then further acts to accommodate minor variations in the size of each patient's chest.

Referring now specifically to FIG. 6, a first internal electrode 60 is provided, the first internal electrode 60 being positioned posterior to the patient's heart 45. The first internal electrode 60 is disposed in the patient's esophagus. Means for positioning the first internal electrode 60 is illustrated in further detail in FIGS. 7, 8, 9, 10 and 11.

Figures 7, 8, 9, 10, 11:
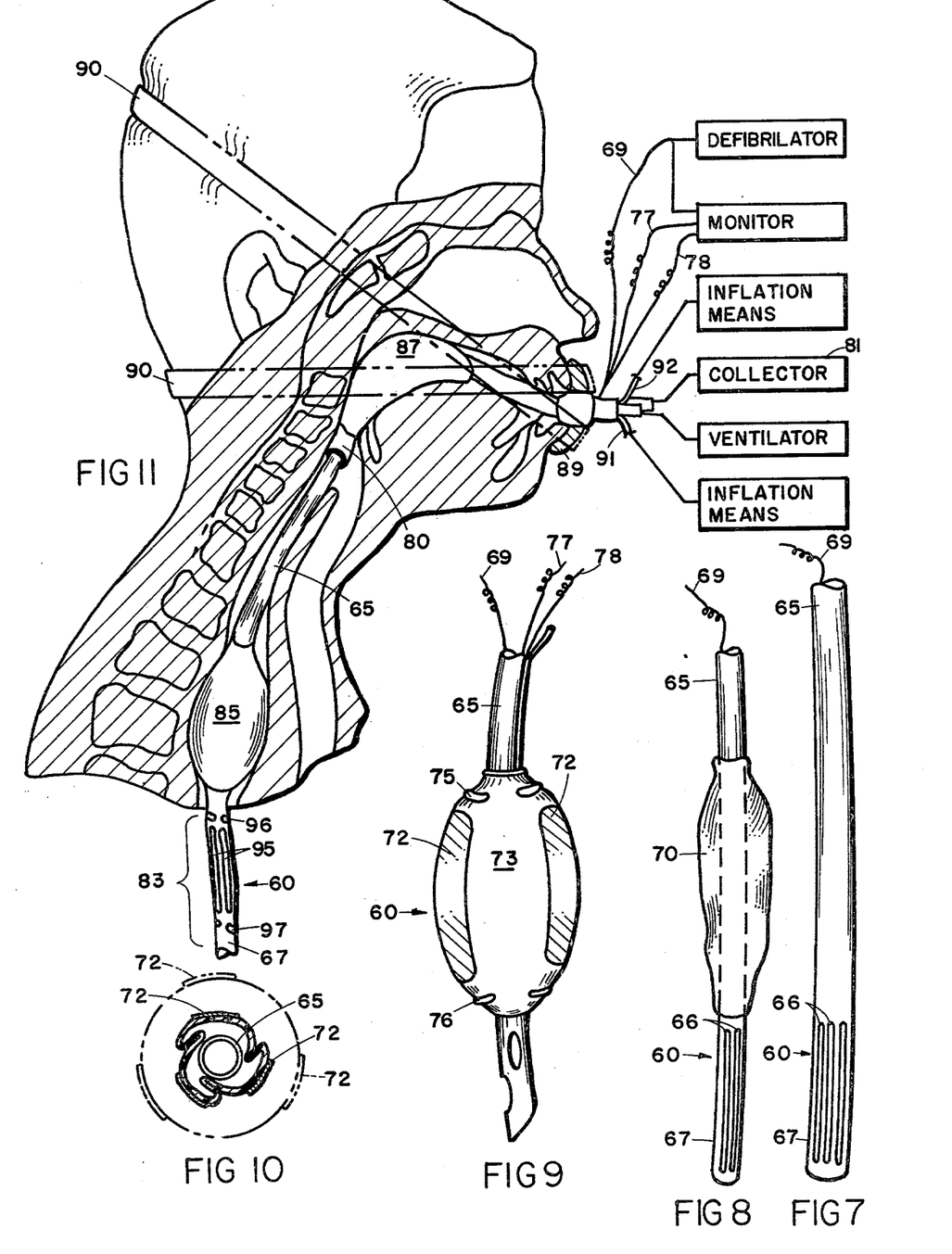
FIG. 7 is a perspective view of an esophageal tube and internal electrode constructed according to the present invention.
FIG. 8 is a perspective view of another embodiment of an esophageal tube and internal electrode constructed according to the present invention.
FIG. 9 is a perspective view of another embodiment of an esophageal tube and internal electrode structure constructed according to the present invention.
FIG. 10 is a sectional view of the esophageal tube illustrated in FIG. 9.
FIG. 11 is a schematic and diagrammatical sagital sectional view illustrating an esophageal-pharyngeal airway of the present invention.

Referring now specifically to FIG. 7, means for positioning the first internal electrode 60 comprises a closed, flexible plastic tube 65 which is insertable in the patient's esophagus. The tube 65 is preferably made of a flexible polymer to facilitate insertion in the patient's esophagus. A flexible first internal electrode in the form of a plurality of metalized strips 66 are disposed on the distal end 67 of the tube 65. The electrode strips 66 may be four to ten centimeters in length. When such a tube is inserted in the patient's esophagus, a good ohmic contact is made with the patient's body during cardiac compression since, as illustrated in subsequent figures, during cardiac compression, the heart and esophagus are compressed against the patient's backbone, ensuring good contact between the electrode strips 66 and the internal surface of the patient's esophagus. The electrode strips 66 may be centered directly behind the patient's heart by connecting an EKG monitor to lead 69 and then varying the position of the tube 65 in the patient's esophagus until the point at which an EKG signal of maximum amplitude is obtained. At this point the electrode strips 66 should be centered directly posterior to the patient's heart and defibrillation may be carried out. It is to be noted that if tube 65 is sufficiently resilient, the tube may be open at both ends such that the tube 65 acts as a gastric drain.

Although the simple esophageal tube 65 may provide an excellent means for defibrillating a patient in ventricular fibrillation, preferably other features are also provided. For example, referring now to FIG. 8, an expandable or inflatable cuff 70 is preferably provided on esophageal tube 65 for sealing the patient's esophagus about the tube 65. The esophageal cuff 70 is preferred since during prolonged, external cardiac compression, the possibility of food and gastric juices escaping the esophagus and being aspirated by the patient is significant. Such an inflatable esophageal cuff 70 may be employed when the tube 65 is hollow and used as a gastric drain. Although in the embodiment of the esophageal tube illustrated in FIG. 8, the inflatable cuff is illustrated as being disposed adjacent the distal end 67 of esophageal tube 65, it is to be understood that the inflatable cuff 70 may be disposed anywhere along the length of esophageal tube 65 to effectively seal the esophagus.

Referring now to FIGS. 9 and 10, another embodiment of an esophageal tube suitable for use with the present invention is illustrated. In this embodiment, a first internal electrode 60 is provided comprising a plurality of flexible metallic strips 72 disposed on the exterior of inflatable cuff 73. The electrode strips 72 are formed of a flexible, highly conductive metal such as silver, gold or copper and since such strips are not stretchable in response to cuff inflating forces, collapse of the cuff involves an overlapping or interleaving of the conductive strips 72 and the non-conductive resilient wall portions of the cuff 73, as best illustrated in FIG. 10. However, it is to be understood that in any of the embodiments of the esophageal tube of the present invention, an impregnation of the resilient and stretchable synthetic rubber or plastic material of the cuff 73 or the esophageal tube 65 may be provided with metallic particles or fibers or the like, thereby providing a wall construction that is both stretchable and conductive. Also, it is to be understood that a conductive polymer, plastic or other elastomer may also be used as an electrode.

In the embodiment of FIG. 9, second and third internal electrodes 75 and 76 are also provided to facilitate centering of the first internal electrode 60. Such orienting and monitoring electrodes 75 and 76 may take the form of small patches or circumferential strips which are positioned on the top and bottom of the outer surface of the cuff 73 and which are insulated from each other and from the electrode strips 72. Leads 77 and 78 extend through the tube 65 to connect the electrodes 75 and 76 to a conventional electrocardiograph or EKG monitor. As before, a lead 69 connects the first electrode strips 72 to monitoring and/or defibrillation circuits. By observing the tracing or electrocardiogram made by the operation of the EKG monitor as the cuff equipped esophageal tube is inserted, an experienced operator may readily determine when the esophageal cuff 73 carrying electrodes 72 has been advanced to the point where it is in direct alignment, i.e., directly centered behind or posterior to the heart. Also, since the EKG electrodes 75 and 76 remain in contact with the esophageal mucosa even when the cuff is inflated, and since only a thin wall of the esophagus separates such electrodes from the heart, cardiac monitoring through the use of such electrodes may be carried out before, during and following trans-esophageal defibrillation. Such an esophageal tube has been disclosed and claimed previously in U.S. Pat. No. 4,090,518 entitled ESOPHAGO-PHARYNGEAL AIRWAY to James O. Elam. The esophago-pharyngeal airway disclosed by Elam therein is suitable for use with the present invention and the disclosure of the aforementioned Elam patent is incorporated herein by reference.

Although a complete esophago-pharyngeal airway as defined in the aforementioned Elam patent is not necessary to practice the present invention, preferably the esophagealpharyngeal airway similar to that illustrated in FIG. 11 of the present application is provided. The esophagealpharyngeal airway of FIG. 11 comprises an esophageal tube 65 which extends through an air tube 80 in a concentric relationship. The esophageal tube 65 is hollow and is connected to a collector 81 for draining food and gastric juices from the patient's stomach. The shorter air tube 80 is connected to the ventilator 15. The collector 81 may be a vomit bag, or a syringe or other device, for introducing fluids to the stomach and flushing or otherwise treating the stomach. The air tube 80 may be connected to any suitable ventilation means but preferably is connected to the integral pneumatically operated ventilation and cardiac compression apparatus illustrated in FIG. 1. The tubes 65 and 80 are formed of a relatively soft, flexible, non-irritating plastic material such as polyvinyl chloride or the like. Although the distal end 67 of the esophageal tube 65 is illustrated as extending past the electrodes 83 and into the stomach to affect a stomach drain, it is to be understood that an esophageal tube 65 may be provided extending just past the electrodes 83.

Preferably, the esophageal-pharyngeal airway illustrated in FIG. 11 is provided with an esophageal cuff 85 for sealing the patient's esophagus about esophageal tube 65 and an oral cuff, or bulbous shape, 87 for sealing the patient's soft palate and nasal passages. A movable oral flange 89 covers the patient's mouth and is secured thereto by straps 90 or other suitable means. One or both of the cuffs may be inflated and deflated through passages or small tubes 91 and 92. The passages 91 and 92 may be connected to suitable inflation means such as a syringe or the like, or alternately, the cuffs may be inflated and partially deflated with each respiratory cycle. In such a latter construction, the repetitiously inflatable and deflatable cuffs are supplied by air from the main air tube or ventilator through ports placing each cuff in communication with the air tube. Such ports put the cuffs in communication with the air tube and are dimensioned so that air supply to the patient first enters and inflates the cuff and when flow is then reversed, air is first extracted from the cuff. These alternate contractions of the cuff allow blood circulation in the area engaged by the cuff and in those constructions where at least the proximal oral sealing cuff is repetiously inflated and deflated permits the exhalation of air through the natural nasal pathway.

The esophageal tube 65 preferably carries a plurality of electrodes generally indicated by the numeral 83. The electrodes disposed at 83 comprise a plurality of longitudinally extending electrode strips 95 which act as the first internal electrode 60 illustrated in FIG. 6. Preferably, this first internal electrode 95 is disposed distally of the esophageal cuff 85 on a portion of esophageal tube 65 since this allows placement of the esophageal cuff 85 anywhere in the patient's esophagus and in fact, allows the placement of the cuff 85 at a higher spot in the esophagus where trauma to the patient due to inflation of the esophageal cuff will be minimized. As previously discussed, the electrode strips 95 may comprise flexible metal strips or a conductive elastomer. Preferably, the first internal electrode 60 is accompanied by second and third internal electrodes 96 and 97 disposed on esophageal tube 65 above and below the first internal electrode 60, respectively. The second and third internal electrodes 96 and 97 are employed to monitor the electrical activity of the heart and to center the first internal electrode 60 with respect to the heart as previously discussed. However, it is to be understood that the first internal electrode 60 may be centered by any one of a variety of techniques, including amplitude monitoring of the electrical activity of the heart as perceived by the first internal electrode 60 and/or by simply gauging the esophageal tube length before it is inserted relative to the patient's sternum, in particular, the patient's zyphoid process which is disposed at the lower end of the patient's sternum. In this case, the esophageal tube 65 would simply be marked at the appropriate point and inserted to ensure an adequate approximate positioning relative to the heart. The electrodes 96 and 97 are each connected via lines 77 and 78 to an EKG heart monitor. The first internal electrode 95 may also be connected to an EKG heart monitor, but it also alternately connectable to a defibrillator for passing a defibrillating electric current through the patient's heart.

Referring now back to FIG. 6, it is illustrated that the external electrode carried on compressor pad 19 is also connected to the defibrillator 100 and/or an EKG monitor 101. In preferred embodiments of the invention, the one external electrode and the three internal electrodes would provide four different positions for monitoring the electrical activity of the heart. It is to be understood that suitable switching means 102 and 103 will be used to isolate the monitor from the defibrillator during defibrillator operation. The invention further includes means for synchronizing the defibrillator and the compressor, preferably comprising a pressure sensitive switch 105 for sensing pneumatic pressure within the power cylinder 17 of the CPR unit 10. The pressure switch 105 acts to disable the defibrillator unit except when pressure within power cylinder 17 reaches a predetermined value. This ensures that the defibrillating counter shock is only applied to the patient's heart during compression of the patient's heart, or during a systolic portion of the compressor cycle. Preferably the pressure switch is set to allow the application of a defibrillating shock only during, or close to, the period of maximum compression in the compressor cycle. However, if the pressure switch is adjustable, the time in the compression cycle during which the defibrillating shock may be applied, may be varied. Adjustability of the pressure switch is also important where it is desirable to only apply the defibrillating shock at the point of maximum compression since the maximum compression pressure will vary with different patients.

It is to be understood that standard defibrillator and monitor circuits may be employed with the present invention although, because of the certain unique advantages presented by the present invention, a defibrillator of much less power than standard defibrillator circuits may be employed. Standard defibrillating circuits include hand-held electrodes or paddles having defibrillating control switches disposed thereon. These standard, commercially available, defibrillating circuits could be modified for use with the present invention by wiring these standard paddle switches or their equivalents in series with pressure actuated switch 105 such that manual actuation of the defibrillator is effective only during the time period when the pressure in power cylinder 17 closes switch 105, indicating that the compressor is in a systolic portion of the compressor cycle.

OPERATION

Referring now to FIGS. 1 and 6, to employ the apparatus of the present invention with a patient requiring cardiac compression for blood perfusion and lung ventilation or blood oxygenization, the patient is placed in the illustrated position (FIG. 6) with his back on platform 12. The cardiac compressor is then adjusted so that the compressor pad 19 is immediately over the lower portion of the patient's sternum 46. Arm 14 of the cardiac compressor is vertically adjusted on columnar support 13 so that the pad 19 contacts the breast bone or sternum when the pad and plunger are in the raised position. A gas supply hose from a conventional source of pressurized oxygen is then connected to the unit at 30. Initially, the cardiac compressor equipment is actuated and adjusted to create the desired chest deflection by adjustment of knob 24 and monitoring of pressure gauge 25. In addition, the esophageal tube 65 carrying first internal electrode 60 is inserted in the patient's esophagus. The first internal electrode 60 may be centered directly below or posterior of the patient's heart 45 by amplitude monitoring of the electrical activity of the patient's heart as perceived by first internal electrodes 60 or by monitoring of second and third internal electrodes 75 and 76 or by simply gauging the length of tube 65 according to the distance between the patient's neck and zyphoid process. With the esophageal tube 65 in place an esophageal cuff may be inflated along with an oral cuff if an air tube is also inserted. If an air tube and oral cuff is not inserted, a simple face mask with or without an oral airway may be employed. At this point, the ventilation subassembly 26 may be actuated and adjusted with adjustment knob 24' while monitoring pressure gauge 25'. A collector may also be connected to the esophageal tube 65 if so desired.

Using one or more of the three internal electrodes and the external electrode disposed on compressor pad 19, effective monitoring of the electrical activity of the heart is provided. In general, the closer the electrodes are to the heart, the stronger the EKG signals are that are received from the heart and the higher the signal to noise ratio of these signals. Thus, the internal electrodes in particular, provide extremely high, strong, very clean signals for monitoring the electrical activity of the heart. Although these signals are slightly distorted by the activity of the CPR unit, these signals are strong and clear enough to detect gross arrhythmias such as ventricular fibrillation. Thus, effective monitoring of the electrical activity of the heart is achieved during normal operation of the supportive CPR unit.

Figure 12:
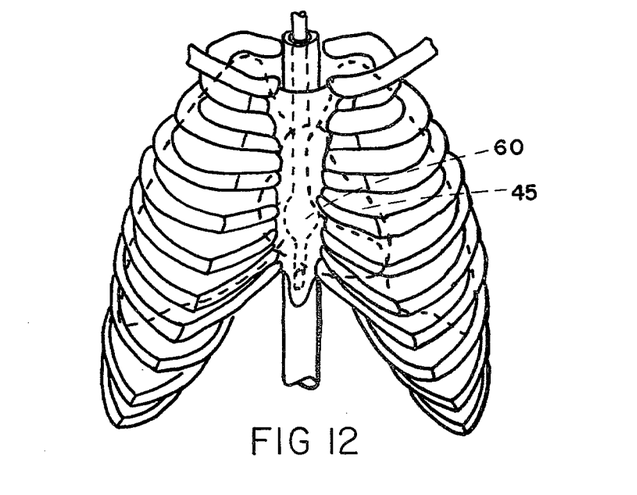
FIG. 12 is a front view of the skeletal structure of the human chest illustrating the relative placement of a patient's esophagus, ribs, sternum, and heart.
Figure 13:
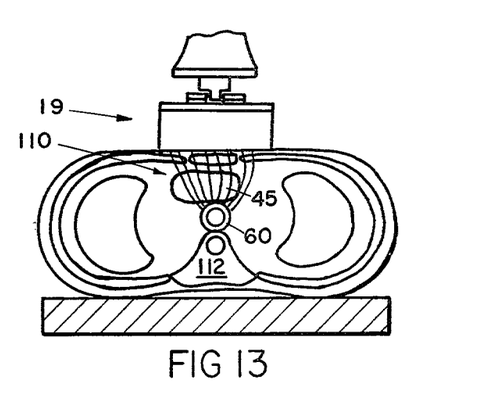
FIG. 13 is a sectional view of the human body and the apparatus of the present invention taken along line XIII—XIII of FIG. 6 during a diastole portion of the compressor cycle.
Figure 14:
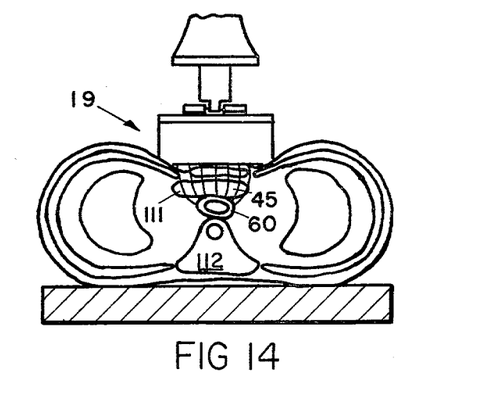
FIG. 14 is a sectional view of the apparatus of the present invention and the human body taken along line XIII—XIII of FIG. 6, except that the cross section is illustrated in a systole portion of the compressor cycle.

When a gross arrhythmia, such as ventricular fibrillation is detected and it is desirable to apply a defibrillation shock to the heart, the combination of the first internal electrode and the external electrode on compressor pad 19 provides a short, direct electrical path through the heart, dramatically reducing the amount of power required to defibrillate the heart. Referring now also to FIGS. 12, 13 and 14, it is illustrated that this electrical path is further shortened by the action of the present invention. Referring now specifically to FIG. 13 illustrating the compressor pad 19 in the diastole position or fully retracted position, the lines 110 represent the electrical conductive path presented by prior art apparatus employing external electrodes and internal esophageal electrodes for defibrillation. Although the electrical paths illustrated by the lines 110 are certainly much shorter than those current paths generated by prior art techniques employing external electrodes, reference to FIG. 14 illustrates that by synchronizing defibrillation shock with the systole portion of the compression cycle, the internal electrode 60 is captured between the heart 45 and the vertebral column 112 to establish intimate contact between the inner electrode and the inner wall of the esophagus and to further substantially decrease the current path between the inner electrode 60 and the outer electrode 48 as illustrated by the lines 111. Thus, in addition to providing a good monitoring path for the electrical activity of the heart during CPR, the present invention provides an improved electrical path for administration of electrical defibrillation shocks to the heart. This dramatically reduces the trauma of electrical defibrillation to the patient by allowing effective defibrillation at reduced levels of total current and thus total electrical energy applied to the patient's body and heart. The efficacy of this technique, using internal and external electrodes as pictured, except for the fact that the external electrode was placed on a compressor pad 19 conforming to the typical shape of a dog chest, has been experimentally verified and both the goals of improved monitoring, and defibrillation with less applied current have been successfully demonstrated. Indeed, these tests have shown that the present invention can successfully defibrillate with levels of applied electrical energy comparable to open heart valves and significantly lower than externally applied electrodes.

Returning specifically now to the description of the operation of the present invention, if, while monitoring the electrical activity of the patient's heart, a gross arrhythmia, such as ventricular fibrillation is detected, the operator may apply definitive therapy such as a defibrillation shock to the patient's heart by simply actuating a manual push button on the defibrillator, the manual push button corresponding to the paddle buttons normally provided on conventional defibrillator paddles. These paddle buttons would simply be depressed until the series wired synchronizing pressure switch 105 closes, determining that a systolic portion of the compression cycle has been reached and triggering the defibrillaton shock. Preferably, the monitor would be temporarily disconnected from the defibrillating electrodes during defibrillation. This can be accomplished by making the switches 102 and 103 automatically actuable by the manually actuable defibrillator push button. As soon as the defibrillation shock has been applied, the monitor may be returned to operation and as the residual effects of the defibrillation shocks subside, an accurate picture of the electrical activity of the patient's heart should again appear. It is to be noted that with the dramatic reduction in the application of electrical energy to achieve defibrillation, the side effects of electrical defibrillation are much less and thus, the monitor clears much quicker, allowing the attendant to immediately determine whether the defibrillation shock has been effective and whether another defibrillation shock is immediately required.

The switch 105 will generally be adjustable such that the operator may precisely time the defibrillation shocks to the point of maximum compression of the CPR unit. Although the operation of the CPR unit need not vary, since it is now being used in conjunction with an electric defibrillator, there are ongoing studies on the state of the art of external cardiac compression, and it may be that more optimal frequencies and dwell times than those employed presently may be achieved in the future. In particular, it is possible that the relationship of ventilation to compression will be optimized a bit differently then that presently used. However, there will always be a finite period of systole in which defibrillation could be accomplished according to the present invention. Because of the dramatically reduced power requirements of a defibrillator operated according to the present invention, it is possible to build defibrillators operating with an expected power requirement of 20 to 30 joules, and probably no more than 50 joules. Thus, one of the major advantages of the present invention is that a defibrillator of very small, compact, low power may be designed which could be powered by rechargable nickel cadium batteries, or the like. The advantages in the portability and the reduction in cost of such a defibrillator should be self evident.

Furthermore, it should be self evident that the apparatus of the present invention provides a unique arrangement for applying both supportive and definitive therapy to a patient in cardiac arrest. More specifically, the apparatus of the present invention provides for simultaneous external cardiac compression and ventilation of the patient while the electrical activity of the patient is continuously monitored for gross arrhythmias and defibrillating shocks are periodically applied directly through the heart's myocardium. Thus, the present invention in addition to improving monitoring techniques and reducing the trauma of defibrillation is unique in its combination of supportive and definitive therapy for cardiac arrest.

The above description should be considered as exemplary and that of the preferred embodiment only. The true spirit and scope of the present invention should be determined by reference to the appended claims. It is desired to include within the appended claims all modifications that come within the proper scope of the invention.

The embodiments of the invention in which an exclusive property or privilege is claimed are defined as follows:

1. A cardiac compressor and defibrillator comprising in combination:
   a reciprocatable cardiac compressor means for cyclically compressing a patient's chest;
   an external cardiac compressor pad for positioning anterior to the patient's heart, said compressor pad being connected to and actuated by said compressor means for compressing the patient's sternum and heart;
   an external electrode disposed on said compressor pad for compression between said compressor pad and the patient's sternum;
   a first internal electrode;
   a means for positioning said first internal electrode in the patient's esophagus, posterior to the patient's heart;
   a cardiac defibrillator means connected to said external and internal electrodes for establishing an electric current therebetween; and
   a means for synchronizing said defibrillator means and said compressor means whereby a defibrillating current is applied to the patient's heart only during compression of a patient's heart.

2. The cardiac compressor of claim 1 further including means for ventilating the patient's lungs.

3. The cardiac compressor of claim 1 wherein said compressor means and said means for ventilating the patient's lungs are pneumatically driven and controlled.

4. The cardiac compressor of claim 1 further including means for monitoring the electrical activity of the patient's heart.

5. The cardiac compressor of claim 1 wherein said means for synchronizing comprises means for sensing pressure applied to the patient's chest by said compressor means and disabling said defibrillator means until a predetermined pressure is reached.

6. The cardiac compressor of claim 5 wherein said means for sensing pressure comprises a pressure sensitive switch for disabling said defibrillator means until a predetermined pressure is reached.

7. The cardiac compressor of claim 6 wherein said defibrillator means is triggered by a manually activated switch said pressure sensitive switch being normally open and connected in series with said manually activated switch to prevent the application of a defibrillating current until a predetermined pressure is reached.

8. The cardiac compressor of claim 6 wherein said compressor means includes a power cylinder and piston; and said pressure sensitive switch is responsive to pressure in said power cylinder.

9. The cardiac compressor of claim 1 wherein said compressor pad is pivotally mounted on said compressor means for accommodating patients with sternums having various angular orientations.

10. The cardiac compressor of claim 1 wherein said compressor pad is provided with a face in contact with the patient's chest, said face having an area greater than approximately eight times the normal heel of hand area applied to the patient's chest during manual CPR.

11. The cardiac compressor of claim 1 wherein said compressor pad comprises an elastomeric body having a face conformable to the patient's chest.

12. The cardiac compressor of claim 11 wherein said external electrode comprises a planar flexible metalized electrode secured to said face of said compressor pad.

13. The cardiac compressor of claim 12 wherein said external electrode presents a contact area of approximately ten square inches with the patient's chest.

14. The cardiac compressor of claim 1 wherein said compressor pad comprises:
a support connected to said compressor means;
a body of flexible closed cell integral skin polyurethane foam mounted on said support;
a face molded into said body, said face being molded to conform to a typical human chest, said body of flexible foam accommodating variations in the size of each patient's chest.

15. The cardiac compressor of claim 14 wherein said external electrode comprises a mesh screen metal electrode vulcanized to said face of said compressor pad.

16. The cardiac compressor of claim 15 wherein a silver mesh screen is provided.

17. The cardiac compressor of claim 15 wherein a gold plated mesh screen is provided.

18. The cardiac compressor of claim 14 further including:
an electrical terminal disposed on said support; and
a plurality of flexible leads interconnecting said terminal and said external electrode.

19. The cardiac compressor of claim 18 wherein said flexible leads run internally in the body of said compressor pad.

20. The cardiac compressor of claim 14 wherein said support comprises a planar metal backing member for supporting said body.

21. The cardiac compressor of claim 20 wherein said planar metal backing member includes a hinge structure for pinning said compressor pad to said compressor means.

22. The cardiac compressor of claim 1 wherein said external electrode is integrally formed with said compressor pad said compressor pad being formed of a conductive material.

23. The cardiac compressor of claim 1 wherein said means for positioning said first internal electrode comprises a flexible tube inserted in the patient's esophagus, said first internal electrode being disposed thereon.

24. The cardiac compressor of claim 23 wherein said flexible tube further includes a inflatable esophageal cuff for sealing the patient's esophagus.

25. The cardiac compressor of claim 24 wherein said flexible tube is open at both ends to provide a passage for gastric drainage.

26. The cardiac compressor of claim 24 wherein said internal electrode is disposed on said esophageal cuff.

27. The cardiac compressor of claim 24 wherein said internal electrode is disposed below said esophageal cuff.

28. The cardiac compressor of claim 23 further including second and third electrodes disposed on said flexible tube, one above said first internal electrode and one below said first internal electrode to facilitate monitoring of the electrical activity of the patient's heart and centering of said first internal electrode posterior of the patient's heart.

29. The cardiac compressor of claim 1 wherein said means for positioning said first internal electrode comprises an esophago-pharyngeal airway.

30. The cardiac compressor of claim 29 wherein said esophago-pharyngeal airway comprises:
a relatively long esophageal tube inserted in the patient's esophagus;
a relatively short air tube inserted in the patient's pharynx;
an esophageal cuff disposed on said esophageal tube for sealing the patient's esophagus;
an oral cuff disposed at the rear of the patient's oral cavity for sealing the patient's nasal passages at the soft palate;
a movable oral flange for sealing the patient's mouth.

31. The cardiac compressor of claim 30 wherein said first internal electrode is disposed on said esophageal tube below said esophageal cuff.

32. The cardiac compressor of claim 31 further including second and third internal electrodes disposed on said flexible tube, one above said first internal electrode and one below said first internal electrode to facilitate monitoring of the electrical activity of the patient's heart and centering of said first internal electrode posterior of the patient's heart.

33. The cardiac compressor of claim 30 wherein said first internal electrode is disposed on said esophageal cuff.

34. The cardiac compressor of claim 30 further including means for ventilating the patient's lungs connected to said air tube.

35. The cardiac compressor of claim 30 further including means for monitoring electrical activity of the patient's heart connected to said first internal electrode and said external electrode.

36. A cardiopulmonary resuscitator and defibrillator comprising in combination:

a reciprocatable cardiac compressor means for cyclically compressing a patient's chest;

an external cardiac compressor pad for positioning anterior to the patient's heart, said compressor pad being connected to and actuated by said compressor means for compressing the patient's heart;

an external electrode disposed on said compressor pad for compression between said compressor pad and the patient's sternum;

an esophago-pharyngeal airway including first and second tubes extending into the patient's esophagus and pharynx, respectively, and means for sealing said first and second tubes in the patient's esophagus and oral cavity, respectively;

a means for ventilating the patient's lungs connected to said second tube;

a first internal electrode disposed on said first tube and positionable posterior to the patient's heart;

a cardiac defibrillator means connected to said external and internal electrodes for establishing an electric potential therebetween;

a pressure sensitive switch for sensing pressure applied to the patient's heart by said compressor means, said switch synchronizing said defibrillator means and said compressor means, whereby a defibrillating current is applied to the patient's heart only during a systolic portion of a compression cycle of said compressor means; and a means for monitoring the electrical activity of the patient's heart connected to said external and internal electrodes.

* * * * *